(12) United States Patent
Kambara et al.

(10) Patent No.: US 6,288,220 B1
(45) Date of Patent: Sep. 11, 2001

(54) DNA PROBE ARRAY

(75) Inventors: Hideki Kambara, Hachioji; Kazunori Okano, Shiki, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/260,543

(22) Filed: Mar. 2, 1999

(30) Foreign Application Priority Data

Mar. 5, 1998 (JP) .................................................. 10-053099

(51) Int. Cl.[7] .................................................. C07H 21/04
(52) U.S. Cl. .................. 536/24.31; 536/24.3; 536/24.32; 536/24.33; 536/25.3; 436/518; 436/523; 436/172; 436/805; 436/809; 422/50; 422/55; 422/64; 422/78; 422/82.05; 422/82.11; 422/99; 204/406
(58) Field of Search .............................. 536/24.31, 24.3, 536/24.32, 24.33, 25.3; 436/518, 523, 172, 805, 809; 422/50, 55, 64, 67, 82.05, 82.11, 99; 435/6, 7.1, 7.5; 204/406

(56) References Cited

U.S. PATENT DOCUMENTS

| 5,804,384 | * | 7/1999 | Muller et al. ............................. 435/6 |
| 5,922,617 | * | 7/1999 | Wang et al. .......................... 436/518 |
| 6,007,987 | * | 7/1999 | Cantor et al. ............................. 435/6 |

OTHER PUBLICATIONS

Science, vol. 251, Feb. 15, 1991, "Light–Directed, Spatially Addressable Parallel Chemical Synthesis", Fodor et al, pp. 767–773.

Analytical Biochemistry, vol. 247, 1997, "Covalent Attachment of Hybridizable Oligonucleotides to Glass Supports", B. Joos et al, pp. 96–101.

Proceedings of the National Academy of Sciences USA, vol. 93, May 1996, "DNA Analysis and Diagnostics on Oligonucleotides Microchips", G. Yershov, et al, pp. 4913–4918.

Biophysical Journal, vol. 71, Aug. 1996, "Scanning Tunneling Microscopy of Mercapto–Hexyl–Oligonucleotides Attached to Gold", D Rekesh et al, pp. 1079–1086.

* cited by examiner

Primary Examiner—W. Gary Jones
Assistant Examiner—Janell E. Taylor
(74) Attorney, Agent, or Firm—Mattingly, Stanger & Malur, P.C.

(57) ABSTRACT

There is used at least one probe array obtained by arraying particles having various probes, respectively, fixed thereon (probe particles) in a definite order in a holder. A plurality of capillaries or grooves packed with various kinds, respectively, of probe particles are arrayed in parallel, and one of particles contained in each capillary or groove is injected into another capillary or groove to produce a probe array in which the various kinds of probe particles are arrayed in a constant and definite order. Various fluorophore-labeled DNA's are measured at the same time by attaching various probes to particles, respectively, of different sizes. A probe array composed of various fixed DNA probes can easily be produced, and there can be provided a probe array for detecting various DNA's which is composed of various fixed arbitrary DNA probes.

14 Claims, 6 Drawing Sheets

DNA PROBE ARRAY

BACKGROUND OF THE INVENTION

1. Field Of The Invention

The present invention relates to a probe array for examining various targets at a time when DNA's, RNA's or proteins are substances to be detected. In particular, it relates to a DNA probe array for DNA detection by hybridization which has recently been the object of attention.

2. Description Of The Related Art

With the advance of the Human Genome Program, there is a strong movement to diagnose diseases and understand life phenomena by understanding living bodies on the basis of DNA. Investigation on the profile of expressed genes is effective in understanding life phenomena and investigating the actions of genes. As an effective means for investigating the gene expression profile, a DNA probe array obtained by fixing a large number of DNA probes for different kinds of the DNA probes separately on a solid surface, or a DNA chip has begun to be used. For producing the chip, there is, for example, a process of synthesizing an oligomer with a designed sequence base by base in each of a large number of enclosed cells by employing a photochemical reaction and a lithography widely used in the semiconductor industry (Science 251, 767–773 (1991)), or a process of spotting DNA probes one by one, respectively, to different cells to make a probe array.

SUMMARY OF THE INVENTION

The key point of the DNA probe arrays is that they are inexpensive and easy to make for any type of probe. The prior art is disadvantageous in this point. The mass production of the DNA probe arrays and the DNA chips requires much labor and time and therefore they are very expensive. Particularly when the density of the cells where the probes are fixed, respectively, in a probe array is large, it is getting difficult to produce the probe array at a low cost. If the size of each cell for a probe species is large, such a probe array is easy to produce but is disadvantageous, for example, in that the volume required for a detection reaction and hence the amounts of samples becomes large as a whole, and in that measurement with the probe array requires much time and does not have high sensitivity.

The present invention was made for removing the above disadvantages, and an object of the present invention is to provide a process which permits easy production of a desired DNA probe array (consisting of DNA probes having desired sequences) with a high density and entails a low production cost.

A DNA probe array has various DNA probes fixed in separate cells, respectively, and target DNA fragments are detected by hybridization with the DNA probes. The target DNA fragments are labeled with a tag such as a fluorophore prior to the hybridization and fluorescence or luminescence and the like are used for the detection of the DNA fragments. The probe array has been used although the density of cells having probes therein is not so high. In the conventional probe array, however, the probes are fixed on each cell that spatially divides the surface of a membrane or the like, and the whole area of the probe array is about 10 cm×5 cm or larger.

On the other hand, the size of the newly developed DNA probe array is about 1 cm×1 cm or less although the number of cells holding DNA probes is very large. The high density probe array is constructed on a solid support such as glass or Si wafer which, together with the high density, is good to reduce the amount of samples consumed for the hybridization. For example, the size of one cell is as small as 0.1 mm×0.1 mm, which should be compared to the conventional size of 5 mm×5 mm. This high density DNA probe array is called a DNA chip. The DNA chip has many cells holding various probes on the surfaces, respectively. It is used for analyzing multiple components in a sample.

In the analysis procedure, at first, all the components in the sample are labeled with tags such as fluorophores or enzymes. They are placed on the DNA chip for hybridization. If the sample has a component being hybridized with probes, the component is held on the corresponding cell. By detecting fluorescence, the position of the cell emitting fluorescence can be determined. From the positional information of the fluorescence emitting cell, the probe species being hybridized with the sample components can be determined. Although the detection and identification of the hybridized position are easy, the production of DNA chips is not so easy because the probe species required for research or testing are changing case by case. In addition, the mass production of the chips is labor intensive and expensive. This is mainly due to the high density production cells in a chip. If the density of cells is as low as the conventional one, the production is relatively easy. The present inventors have found that if the cells can be separately produced and then assembled to make a probe array, the production becomes easy even if the probe components should be changed. The change will be carried out by selecting the cells having probes thereon.

In order to achieve the above object, in the present invention, solid pieces holding probes, respectively, are composed of small particles so as to be movable, and the small particles are sparsely arrayed and then moved to produce a probe array having a dense structure. First, various DNA probes are prepared by synthesis. These DNA probes are fixed on the surfaces, respectively, of small particles (beads), so that the kinds of the DNA probes may be different on the different small particles. A large amount of the DNA probes can be fixed on solid surfaces, respectively, by utilizing a method utilizing the combination of biotin and avidin, a method of fixing DNA probes on Au (gold) surfaces through a SH group (Biophysical Journal 71, 1079–1086 (1996)), a method of fixing DNA probes on glass surfaces (Analytical Biochemistry 247, 96–101 (1997)), a method of fixing DNA probes on an element matrix of acrylamide gel applied on glass surfaces (Proc Natl. Acad. Sci. USA 93, 4913–4918 (1996)), or the like.

The various small particles holding the DNA probes on their surfaces are placed in a holder for examination in a predetermined order so as to indicate the kinds, respectively, of the DNA probes, or the small particles are arrayed and fixed on a solid surface in a predetermined order so as to indicate the kinds, respectively, of the DNA probes, whereby the probe array is produced. The small particles are spherical such as beads. As to their sizes, their diameters range from several micrometers to 1 mm, depending on purpose of use. The small particles may be square, discoidal or the like, depending on purpose of use. For usual examinations, spherical beads with a diameter of 0.1 mm to 0.2 mm can be easily used.

The beads holding the probes, respectively (hereinafter referred to also as "probe beads") are supplied together with a solvent one by one to a groove for producing probe array. Necessary kinds of probes can easily be arrayed in the groove, depending on examinations in which they are used. Since the beads holding the probes, respectively, can be prepared at a low cost, the probe array itself can be produced at a low cost. These beads having the probes attached thereto which have been arrayed in the groove are used after being placed in a capillary for examination or a cell having a narrow space. The employment of a capillary as a probe array holder is advantageous in that the amounts of sample DNA's to be examined can be reduced. It is advantageous also in that the capillary can easily be connected to a solvent-introducing system.

On the other hand, when solid particles having the probes, respectively, fixed thereon are made distinguishable from one another, there is such an advantage that the trouble of arraying the probes by a definite method can be saved.

As explained above, according to the present invention, an arbitrary probe array can be produced easily at a low cost. Moreover, a probe array which reduces the amount of reagents and permits easy injection of the reagents and easy washing can be provided by its construction in a capillary.

Typical examples of the present invention are summarized below. In the typical examples, of the present invention, there is used at least one probe array obtained by arraying particles having various probes, respectively, fixed thereon (hereinafter referred to also as "probe particles") in a definite order in a holder. A plurality of capillaries or grooves packed with various kinds, respectively, of probe particles are arrayed in parallel, and one of the particles contained in each capillary or groove is injected into another capillary or groove to produce a probe array in which the various kinds of probe particles are arrayed in a constant and definite order. Various fluorophore-labeled DNA's are measured at the same time by attaching various probes to particles, respectively, of different sizes. The present invention permits easy production of a probe array composed of various fixed DNA probes, and provides a probe array for detecting various DNA's which is composed of various fixed arbitrary DNA probes.

There are summarized below characteristics of the DNA probe array for examining many items of the present invention and a process for production thereof.

(1) A probe array for examining many items which comprises an array of a plurality of particles having probes, respectively, fixed thereon, said probes being capable of binding to different target substances to be examined (e.g. DNA's, proteins or the like), respectively.

(2) A probe array for examining many items which comprises a plurality of particles having probes, respectively, fixed thereon, said probes being capable of binding to different target substances to be examined, respectively, wherein said particles are arrayed in a line in a predetermined order, and said order is such that the arraying positions of said particles correspond to the kinds, respectively, of said probes fixed on said particles.

(3) A probe array according to the item (2), wherein the sizes or shapes of said particles holding said probes correspond to the kinds, respectively, of said probes fixed on the surfaces of said particles.

(4) A probe array according to the item (2), wherein said particles holding said probes are labeled with different dyes or fluorophores, respectively, depending on the kinds of said probes held by the particles.

(5) A probe array according to the item (2), wherein said probes are arrayed to form a layer on a two-dimensional plane.

(6) A probe array according to the item (2), wherein said particles are one-dimensionally arrayed, and the order of particles (therefore the probes), is predetermined.

(7) A probe array according to the item (2), wherein said particles are held in a container having a transparent window.

(8) A probe array according to the item (2), wherein said particles holding said probes are held in a capillary.

(9) A probe array according to the item (2), wherein said particles holding said probes are held in a groove formed on a flat solid surface or a groove formed between two flat surfaces.

(10) A probe array according to the item (2), wherein said particles holding said probes are two-dimensionally arrayed at a predetermined position(s) by arraying a plurality of capillaries holding said particles holding said probes, or by arraying said particles holding said probes in grooves formed on a flat surface.

(11) A probe array according to the item (2), wherein said particles holding said probes are held in a gel-like substance.

(12) A probe array for examining many items which comprises a plurality of particles having probes, respectively, fixed thereon, said probes being capable of binding to different target substances to be examined, respectively, wherein said particles are arrayed so that characteristics of said particles may correspond to the kinds, respectively, of said probes.

(13) A probe array according to the item (12), wherein the sizes or shapes of said particles holding said probes correspond to the kinds, respectively, of said probes fixed on the surfaces of said particles.

(14) A probe array according to the item (12), wherein said particles holding said probes are labeled with different dyes or fluorophores, respectively, depending on the kinds of said probes held by the particles.

(15) A probe array according to the item (12), wherein said probes are arrayed to form a layer on a two-dimensional plane.

(16) A probe array according to the item (12), wherein said particles are one-dimensionally arrayed.

(17) A probe array according to the item (12), wherein said particles are held in a container having a transparent window.

(18) A probe array according to the item (12), wherein said particles holding said probes are held in a capillary.

(19) A probe array according to the item (12), wherein said particles holding said probes are held in a groove formed on a flat solid surface or a groove formed between two flat surfaces.

(20) A probe array according to the item (12), wherein said particles holding said probes are two-dimensionally arrayed at a predetermined position(s) by arraying a plurality of capillaries holding said particles holding said probes, or by arraying said particles holding said probes in grooves formed on a flat surface.

(21) A probe array according to the item (12), wherein said particles holding said probes are held in a gel-like substance.

(22) A process for producing a probe array which comprises a step of fixing probes on the surfaces, respectively, of particles, and a step of arraying a plurality of said particles having said probes fixed thereon.

(23) A process for producing a probe array according to the item (22), wherein said particles are arrayed on a straight line in a predetermined order so as to indicate the kinds, respectively, of said probes fixed on said particles.

(24) A process for producing a probe array according to the item (22), wherein the plurality of said particles having said different probes, respectively, fixed thereon are transferred to a groove or probe array holder for arraying said particles, by using a plurality of capillaries or grooves for transferring said particles having said probes fixed thereon, and said particles are arrayed on a straight line in a predetermined order so as to indicate the kinds, respectively, of said probes fixed on said particles.

(25) A process for producing a probe array which comprises a step of fixing probes on the surfaces, respectively, of particles, and a step of arraying a plurality of said particles having said probes fixed thereon, as a mixture on a plane, wherein the kinds of said probes fixed on said particles are distinguished by the shapes or sizes or any other physical or chemical properties of the particles or fluorophores labeling said particles, respectively.

(26) A process for producing a probe array according to the item (25), wherein the plurality of said particles having said different probes, respectively, fixed thereon are transferred at the same time to a groove or probe array holder for arraying said particles, by using a plurality of capillaries or grooves for transferring said particles having said probes fixed thereon.

(27) A process for producing a probe array according to the item (25), wherein said particles having said probes fixed thereon are held in different particle reservoirs for the different kinds of said probes, supplied one from each reservoir to a groove for arraying said particles, through a capillary or a groove to be arrayed, and transferred to a probe array holder while maintaining the array, whereby a probe array is produced.

(28) A process for producing a probe array according to the item (25), wherein said particles having said probes fixed thereon are held in different particle reservoirs for the different kinds of said probes, supplied one at a time from each reservoir to a groove for arraying said particles, through a capillary or a groove to be arrayed, and transferred to a probe array holder by means of an electric force while maintaining the array, whereby a probe array is produced.

(29) A process for producing a probe array according to the item (25), wherein said particles having said probes fixed thereon are held in different particles reservoirs for the different kinds of said probes, supplied one at a time from each reservoir to a groove for arraying said particles, through a capillary or a groove to be arrayed, and transferred to a probe array holder by means of a solution flow while maintaining the array, whereby a probe array is produced.

(30) A method for detecting target substances to be examined which bind to probes, respectively,, held on the surfaces, respectively, of particles, said method comprising a step of labeling said target substances with a fluorophore or a material emitting phosphorescence or any tag and a step of irradiating said particles with light (laser beams), followed by optical detection of the fluorescence or phosphorescence emitted.

(31) A method for detecting target substances to be examined according to the item (30), wherein a light source (laser beams) is scanned along a straight line on which said particles are arrayed, and said fluorescence or phosphorescence emitted from tags is detected with an optical sensor.

(32) A method for detecting target substances to be examined according to the item (30), wherein said light (laser beams) is cast along a straight line on which said particles are arrayed, and said fluorescence or phosphorescence emitted from each of the positions at which said particles, respectively, are arrayed, is detected.

(33) A method for detecting target substances to be examined according to the item (30), wherein a pattern of scattering of said light (laser beams) by said particles is obtained by the irradiation with said light (laser beams), fluorescence or phosphorescence emitted from said target substances binding to said probes fixed on said particles is detected, the shapes of said particles or fluorescences emitted by the fluorophores labeling said particles, respectively, are detected, whereby the amounts of said target substances attached to said probes are determined.

(34) A method for detecting target substances to be examined according to the item (30), wherein said particles are detected while being allowed to flow.

(35) A method for detecting target substances to be examined according to the item (30), wherein said target substances attached to said probes fixed on said particles are measured as fluoroscopic images.

(36) A method for detecting target substances to be examined according to the item (30), wherein said particles are measured as two-dimensional images.

(37) A process for producing a probe array which comprises a first step of fixing probes on the surfaces, respectively, of particles, a second step of dividing a plurality of said particles having said probes fixed thereon, into groups and arraying particles in each group in a compartment on a solid surface, and a third step of reacting said probes fixed on said particles with target substances to be examined, in said compartments, wherein the state of distribution of said particles in the first step is different from the state of distribution of said particles in said compartments where said third step is carried out.

(38) A probe array which comprises an array of a plurality of small particles having probes, respectively, thereon, wherein said probes are arrayed one-dimensionally or two-dimensionally, and wherein an order of arrangement of small particles having probes is predetermined, or positions of arrangement of small particles having probes are predetermined.

(39) A probe array according to the item (38), wherein marker particles are placed between the small particles having different kinds of probes. The marker particles are labeled with fluorophores different from the fluorophores labeling the small particles, and the positions of the marker particles on the probe array are reference positions for discriminating the species of the probes on the small particles. (40) A probe array according to the item (38), wherein species of the probes on each of the small particles are different from each other.

(41) A probe array according to the item (38), wherein the small particles include particles having the same species as the probes.

(42) A probe array according to the item (38), wherein each of the probes is capable of binding to DNA, RNA or a protein.

(43) A probe array according to the item (38), wherein the small particles are spherical beads with an outer diameter of 1 $\mu$m to 10 $\mu$m.

(44) A probe array according to the item (38), wherein the small particles are spherical beads with an outer diameter of 10 $\mu$m to 100 $\mu$m.

(45) A probe array according to the item (38), wherein the shape of the small particles is a cubic shape.

(46) A probe array according to the item (38), wherein the shape of the small particles is a cylindrical shape.

(47) A probe array according to the item (38), wherein the small particles are made of glass or plastics

DESCRIPTION OF THE PREFERRED EMBODIMENTS

The examples of the present invention are explained below in detail with reference to the drawings.

FIRST EXAMPLE

Figure 1:
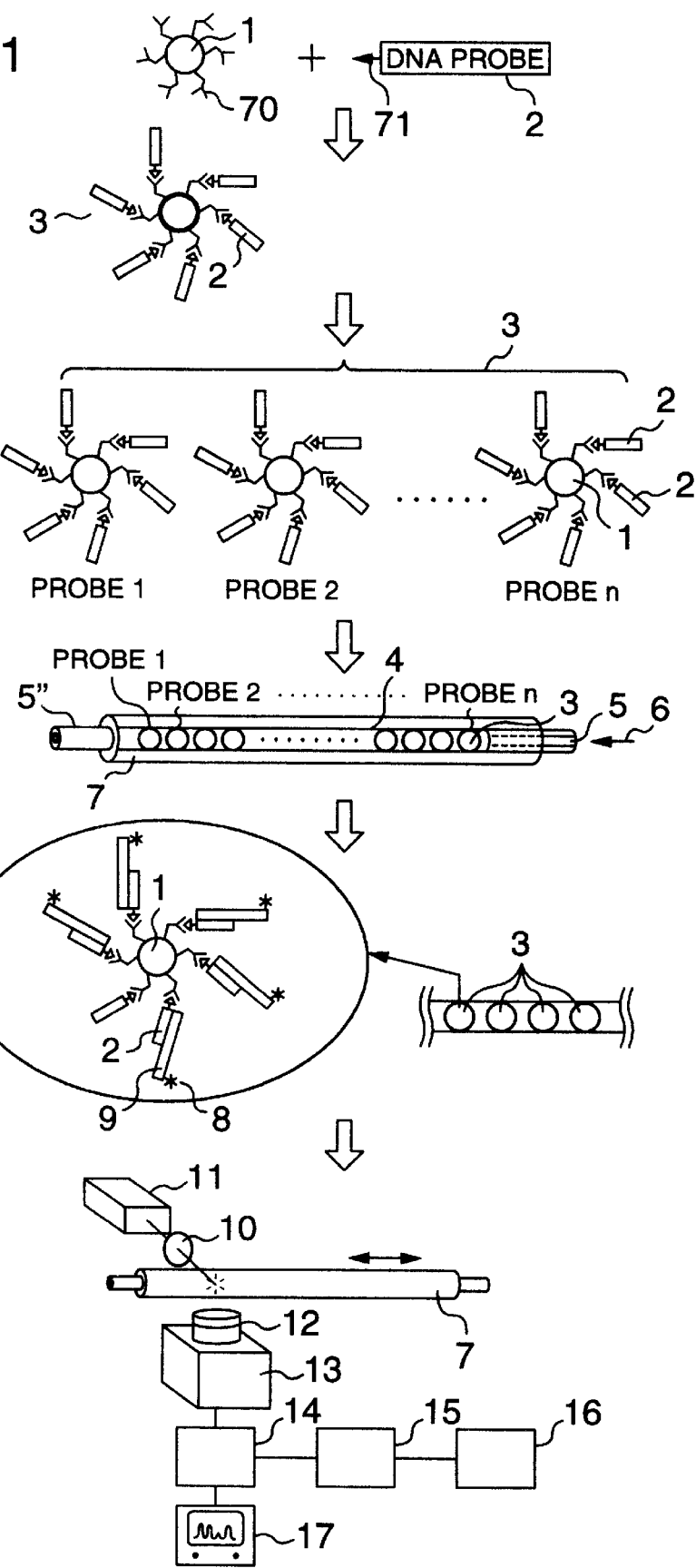
FIG. 1 is a diagram showing a production process of a DNA probe array of a first example of the present invention and an examination apparatus using the DNA probe array.

FIG. 1 is a diagram showing a production process of a DNA probe array of the first example of the present invention and an examination apparatus using the DNA probe array. Spherical plastic particles (beads) 1 (diameter: 0.2 mm) holding avidin 70 on their surfaces are prepared. The precision of diameter of the small particles 1 is 5%. A DNA probe obtained by PCR amplification by using biotin-attached primers is separated into individual strands, and the resulting biotin 71-attached DNA probe 2 is combined with the small particle holding avidin. Thus, each kind of DNA probe is captured by the small particles, respectively, whereby a plurality of groups of small particles attached with probe 3 are formed. Needless to say, synthetic DNA strands may be used as DNA probes. In this case, the DNA probes can be directly attached to solid (small particle) surfaces, respectively, without the combination of biotin and avidin. Methods for attaching DNA probes to solid surfaces, respectively, are described, for example, in the above-mentioned references (Biophysical Journal 71, 1079–1086 (1996) and Analytical Biochemistry 247, 96–101 (1997)). The following method may also be employed: a specific sequence of nucleotides all of which are the same, for example, TTTTT . . . TT is fixed on each solid (small particle) surface, and each DNA oligomer having a poly A strand is hybridized with, the nucleotide sequence to be bonded thereto by binding between complementary strands, whereby the DNA oligomer is introduced onto the solid (small particle) surface.

The thus prepared small particles holding the probes, respectively, are arrayed one by one in a transparent capillary tube (a probe array holder 7) to obtain a probe array 4. The kind of the probe held on the surface of each small particle can be known from the place of this small particle in the order of the small particles arrayed in the capillary tube (the probe array holder 7). Therefore, after hybridization between the DNA probes 2 and sample DNA's having a fluorophore tag 8 attached thereto (numeral 9 shows a sample DNA fragment captured by the small particle 1 by binding between complementary strands), followed by irradiation with light, the kinds of DNA's in a specimen can be known from the fluorescence emitted.

Sample DNA's having a fluorophore tag 8 attached thereto are injected into the capillary tube (the probe array holder 7) containing the probe array 4 composed of probes 1, 2, . . . , n, through the sample inlet 5 of the tube in the sample inflow direction 6 to hybridize the DNA probes 2 with the sample DNA's having the fluorophore tag 8 attached thereto. Then, the probe array holder 7 is set on the movable table (not shown) of the apparatus and laser beams from a laser source 11 are focused by a lens 12 and cast on the moving probe array holder 7. Numeral 5" shows a sample outlet. The color (wavelength) of fluorescence emitted from sample DNA's having the fluorophore tag 8 attached thereto which have been captured by the small particles 1 at positions irradiated with the laser beams is selectively detected by a filter 12 and the photodetector of a CCD (charge coupled device) camera 13 which detects the fluorescence from a direction substantially perpendicular to the direction of the laser beam irradiation. The fluorescence signals thus detected are displayed in real time on a monitor 17. By a data processing unit 15, they are processed to obtain the fluorescence intensity emitted from the particles. The results are displayed on a display unit 16. The axis of abscissa of an output pattern displayed in the monitor 17 refers to the positions of the small particles 1 arrayed in the capillary tube (the probe array holder 7) and hence the kinds of the probes, and the axis of ordinate refers to fluorescence intensity which indicates the presence of the sample DNA fragment bonded to any of the probes by binding between complementary strands. A controller 14 controls the movement of the abovementioned movable table, the incorporation of signals from the CCD camera 13 and the transmission of signals to the data processing unit 15 and the monitor 17. Whether an objective base sequence is present in any of the sample DNA's (DNA fragments) or not can be judged from the output in the monitor 17 or the display unit 16.

It is also possible to carry out the detection by allowing beads to flow together with a solvent instead of moving the capillary tube holding the beads.

Although the fluorophore tag is attached to the sample DNA's (DNA fragments) in the above explanation, it is also possible to attach different fluorophore tags to the probes 1, 2, . . . , n, respectively, instead of attaching the fluorophore tag to the sample DNA's (DNA fragments). In this case, the filter 12 is composed of a many-color filter capable of selecting a plurality of wavelength regions, or wavelengths of fluorescence are separated by using optical prism, a diffraction grating or the like.

Next, a process for producing a probe array using small particles as a probe-supporting medium in the First Example is explained below.

Figure 2A:
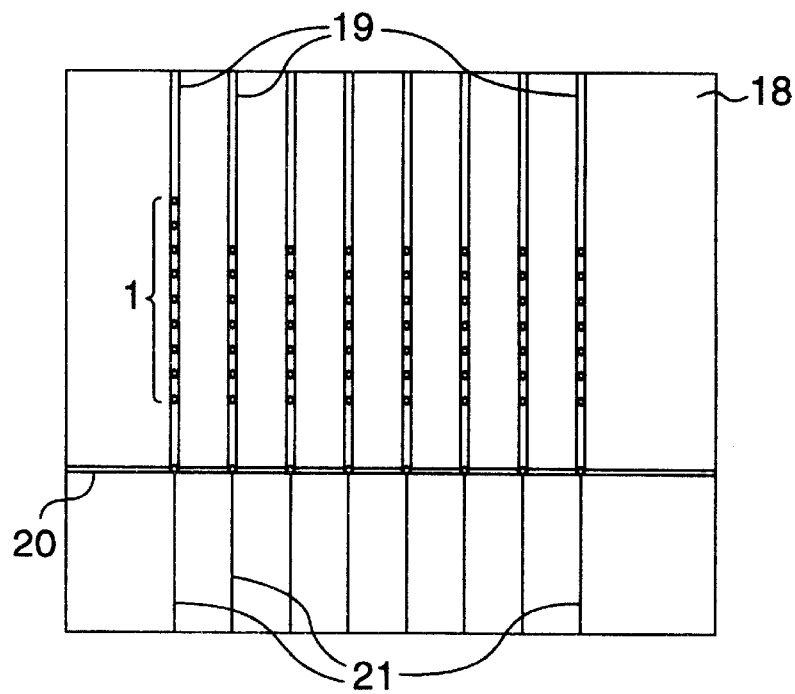
FIG. 2A is a plan view of a plate having fine grooves which is a part of a jig for producing a probe array using small particles as a probe-fixing medium, in the first example of the present invention.
Figure 2B:
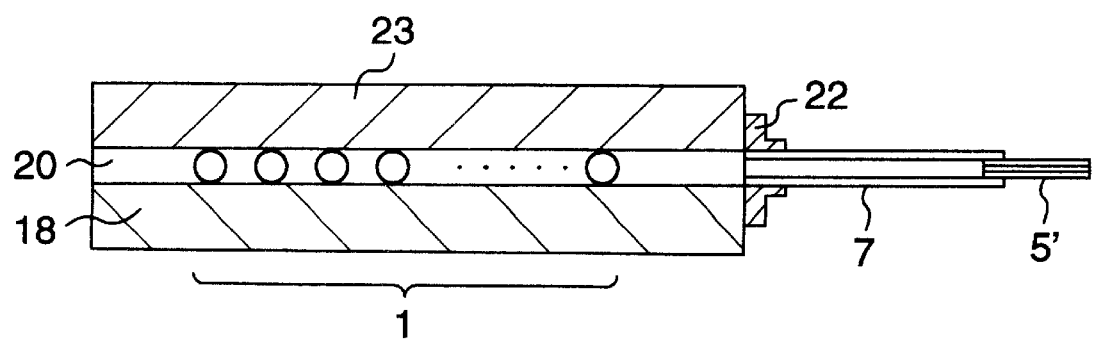
FIG. 2B is a cross-sectional view of the jig for producing the probe array.

FIG. 2A is a plane view of a plate having fine grooves which is a part of a jig for producing a probe array using small particles as a probe-supporting medium, and FIG. 2B is a cross-sectional view of the jig for producing the probe array. Small particles 1 having probes, respectively, attached thereto can be arrayed by means of a device for arraying fine particles by the use of fine grooves. The plate 18 having fine grooves for arraying small particles which is shown in the plan view in FIG. 2A is used after being equipped with the transparent cover 23 which is shown in the cross-sectional view in FIG. 2B. The plate 18 has the following grooves formed thereon: a plurality of grooves 19 for arraying small particles holding different kinds, respectively, of probes in different grooves, respectively; a groove for arraying various probe-holding small particles (a fine groove for producing a probe array) 20 which intersects (is perpendicular to) the grooves 19; and grooves for outlet of solution 21 which discharge a solution. The maximum widths and maximum depths of the grooves 19 and the groove 20 are adjusted to values at which two small particles cannot enter the same groove (namely, the maximum widths and maximum depths satisfy the condition 1 that they should be less than 2R when the diameter of the small particle is taken as R). The maximum width and maximum depth of the grooves 21 are adjusted to values at which the small particles cannot pass the grooves 21 (namely, the maximum width and maximum depth satisfy the condition 2 that they should be less than R when the diameter of the small particle is taken as R). That is, the small particles 1 can pass through capillaries formed by the transparent cover 23 and the fine grooves 19 and 20 formed on the plate 18. As the forms of section of the grooves 19, 20 and 21, any forms may be employed so long as they satisfy the above conditions 1 and 2.

In each of the fine grooves 19, small particles holding the same kind of probes, respectively, are arrayed at random distance intervals. Thus, small particles holding different kinds of probes are divided into groups which are held in the fine grooves 19, respectively. For example, small particles each holding a probe 1 are arrayed in the first groove 19-1 among the grooves 19, small particles each holding a probe 2 in the second groove 19-2, . . . , small particles each holding a probe n in the n-th groove 19-n. Various probe-holding small particles are arrayed in the groove 20 perpendicular to the plurality of the grooves 19. The small particles 1 having probes, respectively, attached thereto are introduced into the groove 20 by a solution flow or an electric field. Since two small particles cannot enter the groove 19 sideways because of their size, each small particle holding various probes, respectively (probe particles) is arrayed at an intersection of the array of plurality of the fine grooves 19 and the groove for arraying probes 20. The grooves 21 after the intersection are so thin that the particles cannot go forward. At this point of time, the distances between two particles are random. The particles arrayed in the groove 20 are introduced into a probe array holding capillary (a probe array holder 7) (inside diameter: 0.3 mm) by a solution flow or an electric field in a direction perpendicular to the grooves 19, namely, along the groove 20 for making an array, to be closely arrayed. Numeral 22 shows a probe array holder connector (a guide device for connecting the probe array and solution inlet as well as outlet) which connects a device for arraying small particles (23 and 20) and the probe array holder 7. Numeral 5' shows a stopper tube. Particles having DNA probes, respectively, fixed thereon which are to be used are supplied to particle reservoirs (see 38 in FIG. 9) communicating with the grooves 19, respectively. The arraying order of the particle reservoirs holding the particles having the probes fixed thereon corresponds to the arraying order of the probes in the groove 20 and the probe array holding capillary. It is also possible to insert a marker between the particles having the probes fixed thereon, for making it easy to know the order.

Next, there is explained an example of the probe array holder 7 which holds probes in a capillary tube, in the First Example.

Figure 3:
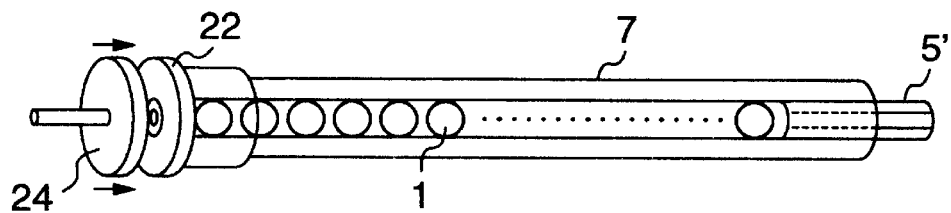
FIG. 3 is a diagram showing an example of a probe array holder in the first example of the present invention.

FIG. 3 is a diagram showing an example of the probe array holder in First Example. Small particles having probes, respectively, attached thereto are held in a probe array holder 7 (a capillary) having a sample inlet and a sample outlet. A terminal adaptor 24 (a terminal adaptor for the capillary holder and the solution outlet) is attached to each end of the probe array holder 7 through a stopper tube 5' and a probe array holder connector (a guide device for connecting the probe array and solution inlet as well as outlet) 22 in order to prevent the outflow of the small particles 1. Needless to say, the adaptor 24 is attached I after introducing the small particles into the capillary (the probe array holder 7).

DNA samples to be examined are labeled with a fluorophore (in this case, Cy-5 (maximum emission wavelength: 650 nm) is used) and introduced together with a solvent into the capillary holding the probe array (the probe array holder 7) to cause hybridization between the DNA samples and the probes. After target DNA's are captured on some of the probes respectively, by the hybridization, the excess DNA samples are washed away, followed by detection of fluorescence. The linear probe array is advantageous in that the probe array holder 7 holding the probe array is easy to scan mechanically, resulting in low consumption of the samples. The fluorophore tag includes Texas Red (maximum emission wavelength: 615 nm), fluorescein isocyanate (maximum emission wavelength: 520 nm), etc. In addition to these fluorophore tags, tags capable of emitting phosphorescence may be used. After the unreacted DNA is washed away, the residue is introduced into a measuring apparatus. The measuring apparatus is composed of a laser for excitation and a fluorescence detector. A large number of the small particles are irradiated at the same time by scanning laser beams along the capillary tube (the probe array holder) or casting laser beams on the interior of the capillary tube along the tube, and the resulting fluorescence images are detected. It is also possible to introduce the small particles one after another into an irradiation portion by moving the capillary tube. In addition, the measurement may be carried out while jetting the solvent and the beads (small particles) through a nozzle, as in a cell sorter.

Next, an example of an apparatus using a DNA probe array is explained below.

Figure 4:
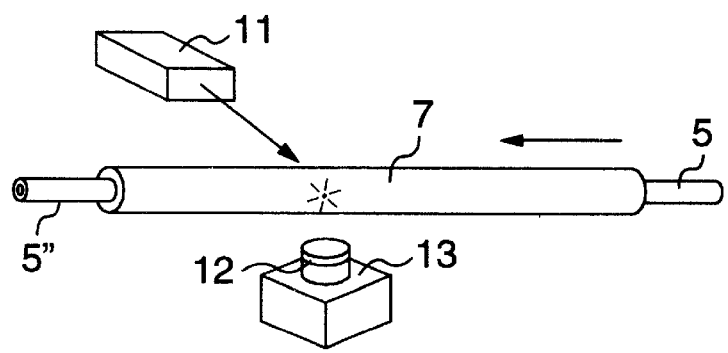
FIG. 4 is a schematic diagram showing an example of an apparatus using a DNA probe array, in which one of the linear probe array and a light source is scanned in relation to the other, in the first example of the present invention.

FIG. 4 is a schematic diagram showing an example of an apparatus using a DNA probe array, in which one of the linear probe array and a light source are scanned in relation to the other. In FIG. 4, the same structure as shown in FIG. 1 is employed, and laser irradiation is carried out as follows: a laser irradiation position and a detector 13 are fixed and a probe array holder 7 holding probes is moved in relation to them; or the probe array holder 7 is fixed, and the laser irradiation position and the detector 13 are moved in relation to the probe array holder 7. As the detector 13, a photomultiplier or a lens-equipped cooled CCD camera is used.

Fluorescence is detected from a direction substantially perpendicular to the laser irradiation direction.

Figure 5:
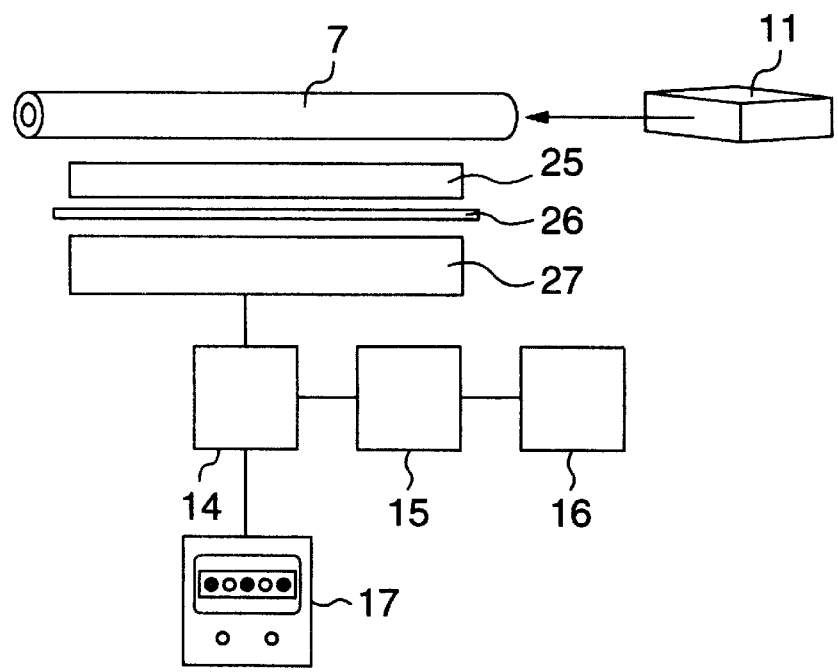
FIG. 5 is a schematic diagram showing an example of an apparatus using a DNA probe array, in which laser beams are cast along a linear array of fine particles, in the first example of the present invention.

FIG. 5 is a schematic diagram showing an example of an examination apparatus using a DNA probe array, in which laser beams are cast along a linear array of fine particles. In FIG. 5, laser beams from a laser source 11 are cast along the axis of a probe array holder 7 in the direction of said axis. Fluorescence emitted by a fluorophore tag is condensed in a microlens-array (Cell Fock Lens (a trade name of Nippon Sheet Glass Co., Ltd.)) 25 and projected on a line sensor (a CCD line sensor) 27 through a filter 26. The other constituents shown in FIG. 5 are the same as those in the structure shown in FIG. 1. Although the structure shown in FIG. 5 is effective, it can be employed only when the small particles are transparent.

Figure 6:
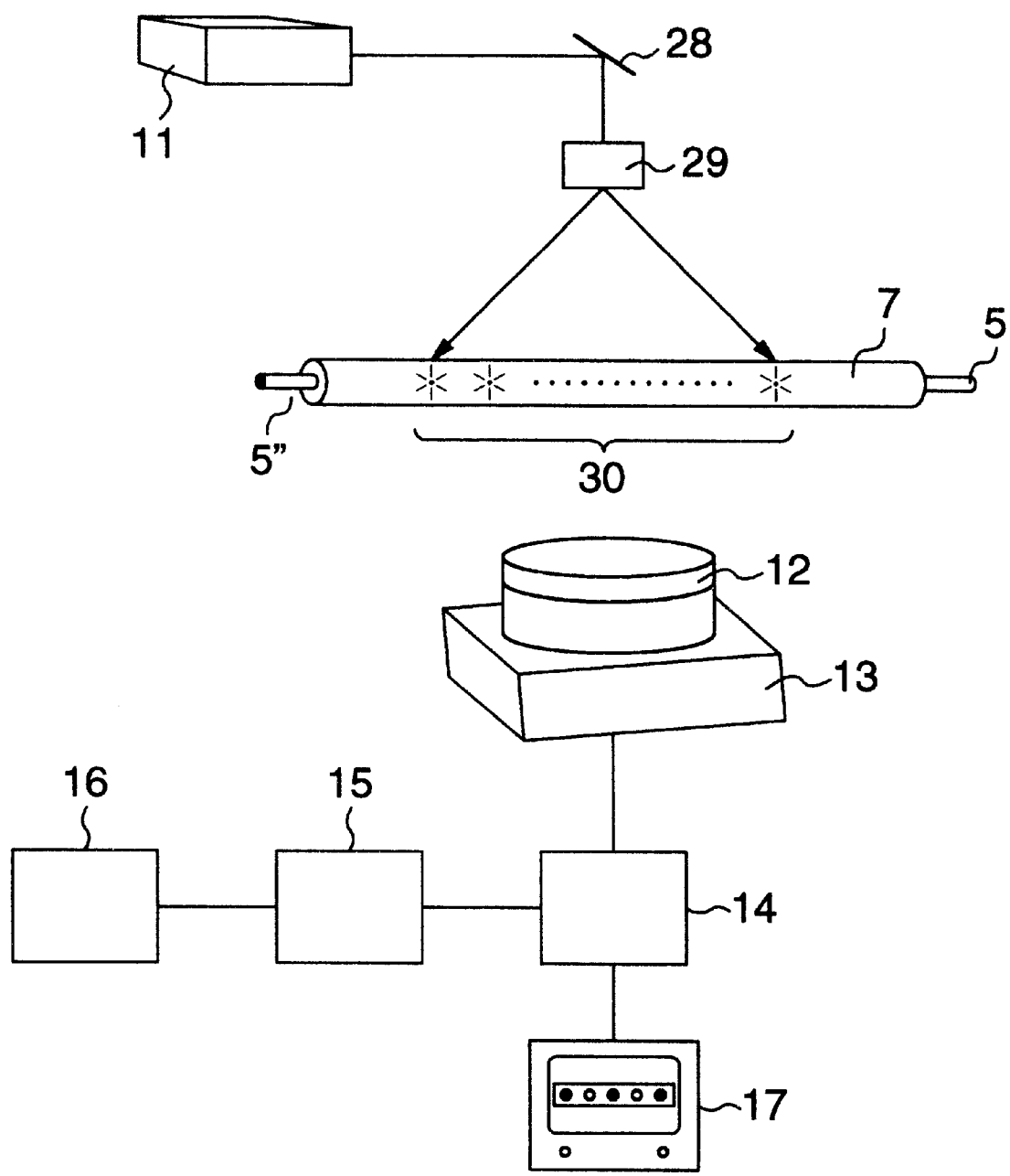
FIG. 6 is a schematic diagram showing an example of an apparatus using a DNA probe array, in which light is cast on the whole of a region where the probe array is present, in the first example of the present invention.

FIG. 6 is a schematic diagram showing an example of an examination apparatus using a DNA probe array, in which light is cast on the whole of a region 30 where the probe array is present (a region where small particles having probes are held and irradiated with laser). Although the probe array is one-dimensional in the structure shown in FIG. 6, a cooled CCD area sensor or the like is used for fluorescence detection so that the examination apparatus can be used also when the probe array is two-dimensional. Laser beams from a laser source 11 change their course at a mirror 28 and the region of irradiation with the laser beams is one-dimensionally expanded by a beam expander 29, whereby the laser beam is cast on the whole of the region 30 where small particles having probes are held and irradiated with the laser, in a probe array holder 7. When a two-dimensional photodetector such as a CCD area sensor is used, two-dimensional fluorescence images are obtained and the kinds of probes are known from the emission positions. The other constituents shown in FIG. 6 are basically the same as in FIG. 1. In FIG. 6, a confocal microscope or a similar technique may be used. For example, instead of using the beam expander 29, laser scanning is carried out by changing the course of the laser beams by rotating the mirror 28, and fluorescence emitted by a fluorophore tag present at a position in the probe array holder on which the laser beams are cast.

Figure 7:
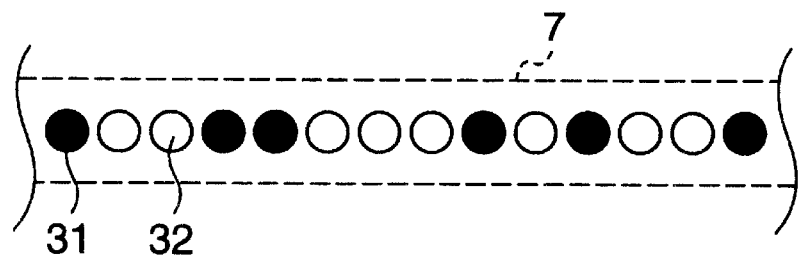
FIG. 7 is a diagram showing an example of results which are obtained by means of the structure shown in FIG. 6 using a small particle type probe array, and which are outputted in a monitor, in the first example of the present invention.

FIG. 7 is a diagram showing an example of results which are obtained by means of the structure shown in FIG. 6 using a small particle type probe array, and which are output in a monitor 17. In the example shown in FIG. 7, a small particle 31 emitting fluorescence (a small particle attached with target DNA) is shown by a closed circle, and a small particle 32 not emitting fluorescence (a small particle not attached with target DNA) is shown by an open circle. The fluorescence intensity is high at the closed circles 31, indicating that DNA's are captured by probes. Although sample DNA's are labeled with a single fluorophore in the example shown in FIGS. 6 and 7, it is also possible to label a plurality of specimens for examination of DNA's with a plurality of fluorophores, respectively, and carry out comparative measurements.

As explained above, when DNA probes held by particles are held in a capillary, there are advantages such as easy supply of samples and easy washing. Moreover, there are advantages such as easy fluorescence measurement, easy production of a necessary desirable probe array, and provision of an inexpensive probe array. In addition, the volume of samples which is required for hybridization can be reduced. Although a capillary is used for holding a plurality of probes in the First Example, a groove formed on a transparent and flat plate may also be used. When particles are arrayed in the groove, the following is possible: a gel is held in the bottom of the groove, and particles holding probes, respectively, are arrayed in the groove and then fixed on the gel by pressing thereon. In this case, a space to be filled with a sample solution is reduced, so that the consumption of the samples can be reduced. Needless to say, also when a probe array is produced using a transparent and flat plate having a groove formed thereon, the example of the examination apparatus shown in any of FIG. 1, FIG. 4, FIG. 5, FIG. 6 and FIG. 10 (hereinafter described) can be used, and samples captured by probes can easily be detected by fluorescence.

SECOND EXAMPLE

In the First Example, the probe array is formed on a straight line. In the Second Example, an example of a two-dimensional arrangement of probe arrays is given. Small particles used in the Second Example have the same diameter of 0.2 mm as that in the First Example. When particles with a diameter of 0.1 mm or 0.05 mm or less than 0.05 mm are used, it is necessary to change the pitch and depth of grooves and the size of a probe array holder which are described hereinafter. Particles of various sizes ranging from 1 $\mu$m to 100 $\mu$m in diameter are supplied for the use.

For the two-dimensional arrangement of probe arrays, there is used either a probe array holder obtained by arraying capillaries holding probe arrays, respectively, or a probe array holder obtained by forming a plurality of grooves on a flat plate and attaching a transparent cover to the flat plate. A process for producing a probe array holder for a two-dimensional array of probe arrays by arraying capillary tubes is the same as the production process of a probe array holder in the First Example, except that a plurality of capillaries are merely arrayed. However, a housing for holding the plurality of the capillaries in parallel, supplying samples and introducing a wash liquid should be modified so as to be suitable for the multi-capillary. When laser beams are cast on the plurality of capillaries, it is preferable to adopt either a method comprising casting laser beams from a direction parallel to a plane on which the capillaries are arrayed, and detecting fluorescence emitted in each capillary with a two-dimensional detector, or a method comprising casting laser beams two-dimensionally expanded by a beam expander, with scanning, or carrying out light irradiation by light scanning of laser beams condensed into a point, and detecting fluorescence emitted in each capillary with a two-dimensional detector.

A probe array holder obtained by forming a plurality of grooves on a flat plate is explained below. A two-dimensional probe array holder (a holder having probes arrayed in two-dimensional area) 34 is composed of a cell having a space of 0.1 mm between two transparent flat plates, the lower of which has grooves. Each groove has a pitch of 0.3 mm, a width of 0.25 mm and a depth of 0.15 mm. Both the width and depth of the groove are too small for the passage of two particles and are sufficient for the passage of one particle. Small particles having probes, respectively, fixed thereon are arrayed in each groove. The small particles have a diameter of 0.2 mm and cannot move from one groove to another groove.

Figure 8A:
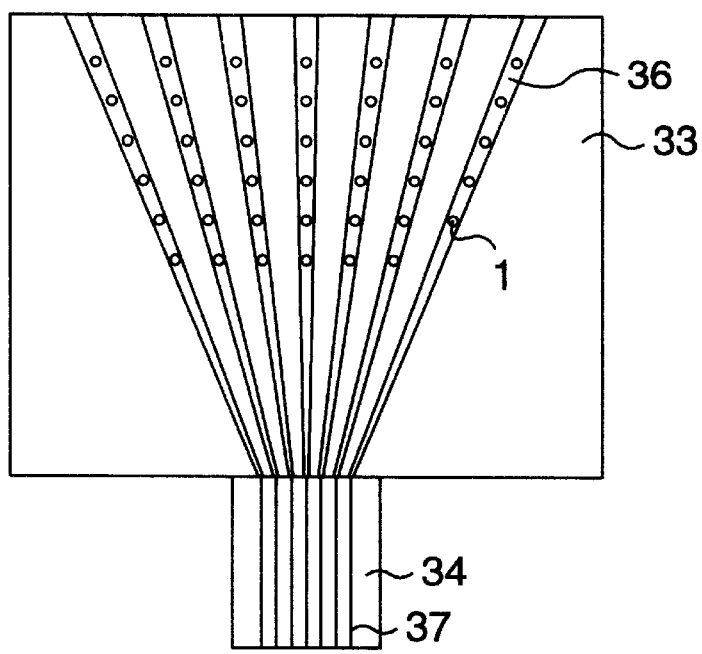
FIG. 8A is a plan view of a jig for introducing small particle holding probes, respectively, into a two-dimensional probe array holder (a holder having probes arrayed in a two-dimensional area) 34, in a second example of the present invention.
Figure 8B:
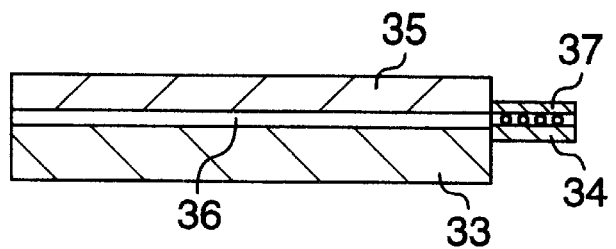
FIG. 8B is a cross-sectional view of the jig.

FIG. 8A is a plan view of a jig 33 for producing a two-dimensional probe array for introducing small particle holding probes, respectively, into a two-dimensional probe array holder (a holder having probes arrayed in two-dimensional area) 34, and FIG. 8B is a cross-sectional view of the jig. For arraying small particles in the two-dimensional probe array holder 34, guide grooves 36 for arraying small particles in cell are used. The openings of the grooves 36 are covered with a transparent cover 35. As shown in FIG. 8A, each groove 36 is widened toward the end, and small particles (beads) 1 having probes, respectively, attached thereto are arrayed in the wide portion of the groove 36 in a predetermined order so as to indicate the kinds, respectively, of the probes held by the small particles. The small particles 1 having probes attached thereto which have been arrayed in the array of the grooves 36 are moved to the narrow portions (particle-holding portions) of the grooves 36 by a solvent flow or an electric field to be transferred to the two-dimensional probe array holder 34. As shown in the cross-sectional view shown in FIG. 8B the small particles having probes attached thereto which have been sparsely arrayed in the grooves 36 are held in the two-dimensional probe array holder 34 in a closely arrayed state. The probe array holder 34 has openings (not shown) for introducing and draining, respectively, a sample solution or a wash liquid. The above array of the small particles having probes attached thereto in the grooves 36 is carried out by, as in the First Example, arraying the small particles in capillaries at first and transferring them to the grooves 36. Since small particles in any of the grooves 36 cannot move to the adjacent groove 36, different groups of probe particles are arranged in different arrays (different grooves). The order of the probes in each array (each groove) can be determined in the same manner as in the First Example. Then, the small particles are transferred to fine grooves 37 for keeping fine particles attached with the probe, from the grooves 36.

The apparatus shown in FIG. 6 is modified for detecting two-dimensional probe array holder 34. In the modified apparatus, as shown in FIG. 6, one-dimensionally expanded laser beams are linearly cast on the two-dimensional probe array holder 34, and laser beams are linearly scanned in a direction perpendicular to the direction of the expansion. The two-dimensional fluorescence images thus obtained are detected using a two-dimensional detector (e.g. CCD). Needless to say, it is also possible to obtain two-dimensional fluorescence images by two-dimensionally scanning laser beams condensed into a point.

THIRD EXAMPLE

A key point of the process of the present invention is a method for easily arraying small particles. In this Third Example, there is described an example of production of a probe array by an easy method to array small particles. In a probe array, a close array of solid pieces (particles) holding probes, respectively, is important in reducing the reaction volume and facilitating the measurement. On the other hand, the production of a probe array is easier when the probe-holding positions are scattered. Accordingly, the point of the present invention is to employ a structure in which the probe-fixing positions are movable, and to densify the structure after the formation of a probe array. That is, the point of the present invention is to move solid pieces (particles) having probes, respectively, fixed thereon, and thereby produce a probe array composed of a tight array of the solid pieces (particles) having probes fixed thereon.

For arraying small particles holding various probes, respectively, on their solid surfaces (probe particles), there is a method of arraying the small particles one by one in the groove of a probe array holder with tweezers or the like. This method is similar to a method employed for producing a probe array by attaching probes to the separate cells, respectively, on a continuous solid surface. This so-called spotting becomes more difficult as the region of each probe becomes finer. However, it is possible to finely array independent small particles having probes, respectively, attached thereto. For example, to produce a probe array composed of a tight array of solid pieces (particles) having probes, respectively, fixed thereon, the following is sufficient: first, small particles having probes, respectively, attached thereto are sparsely placed in the grooves shown in FIG. 2 or the grooves shown in FIG. 8, and are moved by a solution flow, an electric field or the like to form a tight array, which is held in a probe array holder 7 or 34.

Figure 9:
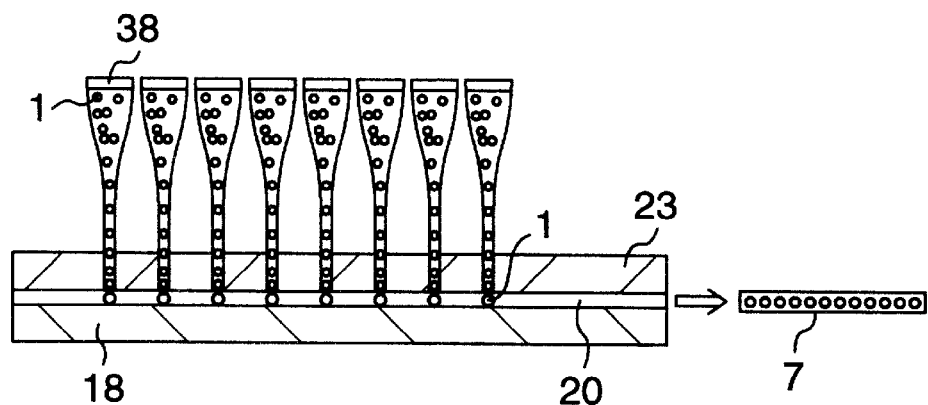
FIG. 9 is a schematic illustration of an example of a method for introducing small particles holding probes, respectively, into a groove for array from small particle reservoirs, in a third example of the present invention.

FIG. 9 is a schematic illustration of an example of a method for introducing small particles holding probes, respectively, into a groove for array from small particles reservoirs. In the probe array production process shown in FIG. 9, from each reservoir holding a large number of the same kind of small particles having probes, respectively, attached thereto, the small particle is supplied to a groove. In FIG. 9, the small particle 1 is supplied from each reservoir 38 of the small particles 1 to a groove (20 in FIG. 2) through fine grooves (19 in FIG. 2) by a solution flow to be transferred to a probe array holder 7. The following is also possible: similarly, the small particle 1 is supplied from each reservoir 38 of the small particles 1 to a groove (36 in FIG. 8) by a solution flow to be transferred to a probe array holder 34. The reservoirs 38 of the small particles may be perpendicular to or on a plane on which the grooves 19 or 36 are formed, though in the Third Example, a convenient structure can be obtained when the particle reservoirs 38 are perpendicular to the plane and are mountable and demountable. This is because the kinds of the probes can be freely changed depending on purposes. In the particle array, the probe species on the particles are recognized by their positions in the array.

FOURTH EXAMPLE

In this Fourth Example, small particles having probes, respectively, attached thereto are arrayed according to a predetermined order, and the probe species can be recognized by the particle positions. In the First to Third Examples, the kinds of probes held by small particles, respectively, are distinguished by the positions at which the small particles are held, respectively, though the Fourth Example discloses a method for distinguishing the kinds not by the positions of the small particles under observation but by the shapes (e.g. particle diameter), dielectric properties, electromagnetic properties or colors of the small particles themselves. That is, this method is such that in obtaining signals from fluorophore-labeled samples captured by probes, the kinds of the probes on the surfaces of particles are investigated at the same time by measuring the shapes, colors or the like of the particles. It is also possible to label particles with one or more fluorophores that are different in kind from the fluorophore labeling the samples.

In this Fourth Example, there is described a case of labeling samples with a long-life fluorophore or phosphor tag, and distinguishing small particles by the differences among their sizes and the difference among fluorescences emitted by fluorophores labeling the small particles, respectively. As the fluorophores for distinguishing the small particles, there are used fluorophores having a relatively short fluorescence life, such as FITC, Texas Red, Cy-5, etc. The reason why the particles are labeled with the fluorophores having a relatively short fluorescence life is that the distinction of fluorescences emitted by the fluorophores labeling the particles from fluorescence emitted by the fluorophore with a long fluorescence life used for labeling the samples is made possible. Needless to say, it is also possible to carry out the distinction by changing the fluorescence wavelengths.

Figure 10:
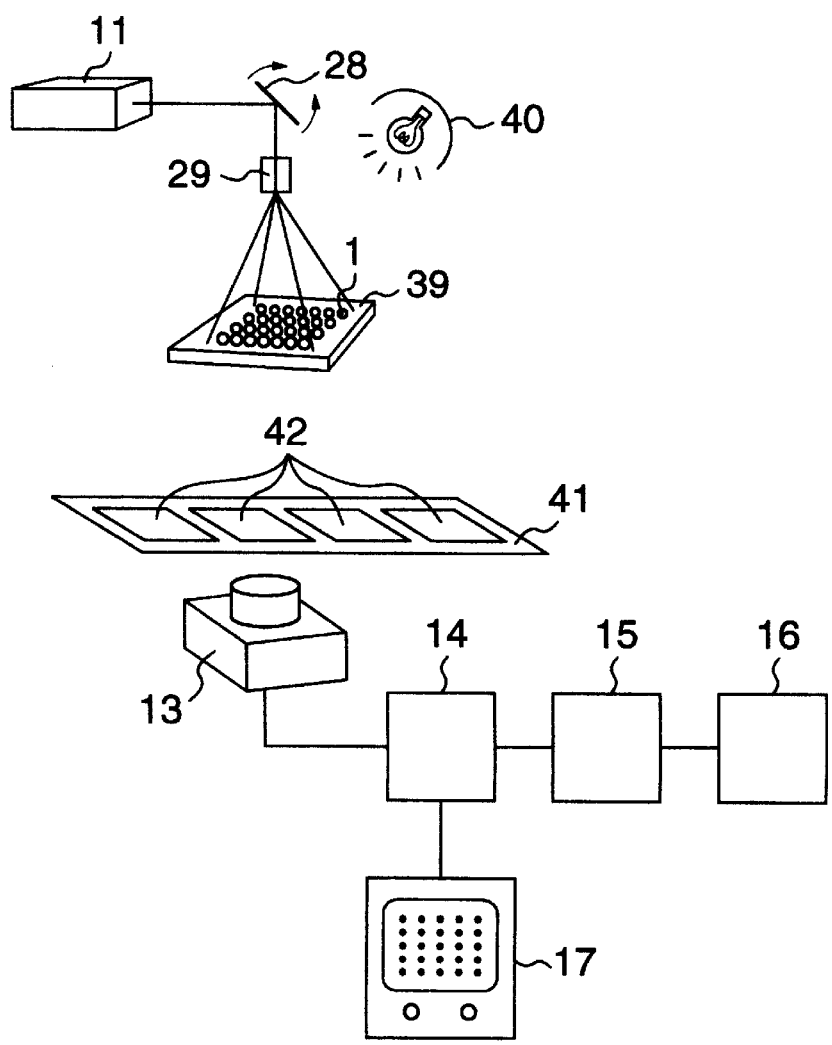
FIG. 10 is a schematic diagram showing the structure of an examination apparatus in which samples are detected by detection of many colors by the use of a two-dimensional probe array, in a fourth example of the present invention.

FIG. 10 is a schematic diagram showing the structure of an apparatus in which samples are detected by detection of many colors by the use of a two-dimensional probe array. FIG. 10 shows a case of using a plurality of filters. First, light from a flash lamp 40 is cast on a probe array 39 composed of a two-dimensional array of small particles 1 having probes, respectively, attached thereto which have been reacted with samples, the light transmitted by a transparent supporting table for the probe array 39 is passed through a light attenuation filter if necessary, signals detected by a CCD (charge coupled device) camera 13 are input to a data processing unit 15, it is confirmed that the particles do not overlap in the probe array 39, and the shapes of the particles (beads) are measured.

Subsequently, laser beams 11 from a laser source are cast on the probe array 39 by a rotary mirror 28 capable of scanning the laser beams in a first direction, and a beam expander 29 capable of expanding the irradiation region of the laser beams in a second direction perpendicular to the first direction. Fluorescences having various wavelengths are selected and separated while changing the transmission wavelength by sliding a plurality of fluorescent wavelength selective filters 42 held by a slide-type or rotary-type filter holder 41. After being separated, the fluorescences emitted from the probe array 39 are detected by the CCD camera 13 or array detector. The controller 14 controls the rotary mirror, the flash lamp 40, signal incorporation from the CCD camera 13, and signal transmission to the data processing unit 15 and a monitor 17. Whether an objective base sequence is present in any of the sample DNA's (DNA fragments) can be judged from the output in the monitor 17 or a display unit 16.

In the Fourth Example, mixtures of two fluorophores in various ratios are attached fast to surfaces, respectively, of small particles. Thus, as many as 20 small particles are distinguished by mixtures of each pair of fluorophore by varying the mixing ratio. For example, when fluorophores F1 and F2 are used and the mixing ratio between these fluorophores F1 and F2 is taken as (w1, w2), 20 ratios are selected as the mixing ratio (w1, w2) from the following ratios: (w1, w2)=(0, 0.05), (0.05, 0.95), (0.1, 0.9), (0.15, 0.85), (0.2, 0.8), (0.25, 0.75), (0.3, 0.7), (0.35, 0.65), (0.4, 0.6), (0.45, 0.55), (0.5, 0.5), (0.55, 0.45), (0.6, 0.4), (0.65, 0.35), (0.7,0.3), (0.75, 0.25), (0.8, 0.2), (0.85, 0.15), (0.9, 0.1), (0.95, 0.05), and (1.0, 0). When these ratios are independently changed, about 100 particles can be distinguished. On the other hand, by the use of groups of particles which have 15 particle sizes, respectively, of 100 $\mu$m to 198 $\mu$m that are different by 7 $\mu$m each, the particles in the groups, respectively, are distinguished by their sizes. In the measuring apparatus shown in FIG. 10, the sizes of the small particles and fluorescences are measured. In this apparatus, exciting light is cast in pulses, and longlife phosphorescence emitted by the tag labeling DNA's and fluorescences emitted by the tags labeling the particles can be measured in distinction from each other in a time-divided manner. Needless to say, the difference in wavelength may be utilized. In this case, it is preferable to employ fluorescence wavelength ranges that are different from the phosphorescence wavelength range. Thus, 300 (20×15) kinds in total of DNA probes (particles) are distinguished at the time of the measurement. As a measuring apparatus, there is used a laser scanning type fluorescence-detecting apparatus or a received-light wavelength selection type cooled CCD. As a wavelength selector, there can be used a diffraction grating, a wavelength-dispersing prism, or a spectroscopic system composed of a plurality of band-pass filters.

The kinds of the particles are distinguished by the relative intensities of the fluorescences measured. A large number of particles with the same particle diameter can be distinguished by varying the wavelength of the exciting light (laser beams). For example, when particles are labeled with mixtures of Joe and Tamura (fluorophores excitable by means of a YAG laser) in various ratios, about 10 kinds of particles can be distinguished by estimating in 10 grades the ratio between the intensities of signals obtained from two filters, respectively, adjusted to optimum light-receiving channels for signals from the fluorophores. On the other hand, when particles are labeled with Rox in addition to Joe and Tamura, 30 kinds in total of particles with the same particle diameter can be distinguished by the following mixing ratios of the fluorophores: 10 mixing ratios between Joe and Tamura, 10 mixing ratios between Joe and Rox, and 10 mixing ratios between Tamura and Rox. Moreover, when samples are labeled with five fluorophores which emit fluorescence having a long wavelength and can be excited by means of a semiconductor laser, 150 kinds of samples can be distinguished. Furthermore, when size measurement using particles having 15 particle diameters is combined with the above measurements, 2,250 kinds of DNA probes can be distinguished. Since the particles hold different probes, respectively, on their surfaces, 2,250 kinds of DNA's can be distinguished and detected. When a container for probes is partitioned into compartments, or there is used a holding chip having a plurality of sites (compartments) in which the groups, respectively, of particles explained above are held, particles holding different groups of DNA probes can be held in different divisions (compartments), so that the number of distinguishable DNA's can easily be increased to 10,000 or more.

Although particles are labeled with fluorophores in the above explanation, dyes may be used for the labeling. Since the kinds of probes can be freely varied depending on purposes, a multi-probe sensor device suitable for various purposes can be obtained.

The above names Joe, Tamura and Rox are trade names given by Perkin-Elmer ABD Corporation, Texas Red is a trade name given by Molecular Probe Co., Ltd., and Cy-5 is a trade name given by Amersham Pharmacia Biotech Ltd.

What is claimed is:

1. A probe array for analyzing target substances which comprises an array of a plurality of spherical particles having probes, respectively, fixed thereon, said probes being capable of hybridizing to different target substances to be analyzed, respectively, and said particles are arrayed in a single straight line in a transparent capillary, wherein the species of each of said probes can be known from the place of each of said particles in the order of each of said particles arrayed in said single straight line.

2. A probe array for analyzing target substances which comprises a plurality of spherical particles having probes, respectively, fixed thereon, said probes being capable of hybridizing to different target substances to be analyzed, respectively, wherein said particles are arrayed in a single straight line in a predetermined order in a transparent capillary, and said order is such that the arraying positions in said straight line of said particles correspond to the species, respectively, of said probes fixed on said particles.

3. A probe array according to claim 2, wherein said particles holding said probes are labeled with different dyes or fluorophores, respectively, depending on the species of said probes held by the particles.

4. A probe array according to claim 2, wherein said particles holding said probes are two-dimensionally arrayed at predetermined positions by arraying a plurality of capillaries holding said particles holding said probes.

5. A probe array for analyzing target substances which comprises a plurality of spherical particles having probes, respectively, fixed thereon, said probes being capable of hybridizing to different target substances to be analyzed, respectively, and said particles are arrayed in a single straight line in a transparent capillary, wherein said particles are arrayed so that positions of said particles in the single straight line may correspond to the species, respectively, of said probes.

6. A probe array according to claim 5, wherein said particles holding said probes are labeled with different dyes or fluorphores, respectively, depending on the species of said probes held by the particles.

7. A probe array according to claim 5, wherein said particles holding said probes are two-dimensionally arrayed at predetermined positions by arraying a plurality of capillaries holding said particles holding said probes.

8. A probe array which comprises an array of a plurality of small spherical particles having probes, respectively, thereon, wherein said particles are arrayed in a single straight line in each of a plurality of transparent capillaries and said probes are arrayed two-dimensionally, and wherein an order of arrangement in said single straight line of the small spherical particles having probes is predetermined, or positions of arrangement in said single straight line of the small spherical particles having probes are predetermined.

9. A probe array according to claim 8, wherein marker particles are placed between the small spherical particles having different species of probes.

10. A probe array according to claim 8, wherein species of the probes on each of the small spherical particles are different from each other.

11. A probe array according to claim 8, wherein the small spherical particles include particles of the same species as the probes.

12. A probe array according to claim 8, wherein each of the probes is capable of binding to DNA, RNA or a protein.

13. A probe array according to claim 8, wherein the small spherical particles are spherical plastic particles.

14. A probe array for analyzing target substances which comprises a plurality of spherical particles having probes, respectively, fixed thereon, said probes being capable of hybridizing to different target substances to be analyzed, respectively, and said particles being arrayed in a single straight line in a transparent capillary, wherein an inside diameter of said capillary is too small for the passage of two particles and is sufficient for the passage of one particle.

* * * * *